(12) United States Patent
Zhao et al.

(10) Patent No.: US 9,949,914 B2
(45) Date of Patent: Apr. 24, 2018

(54) LOW VISCOSITY HAIR CARE COMPOSITION

(71) Applicant: The Procter & Gamble Company, Cincinnati, OH (US)

(72) Inventors: Jean Jianqun Zhao, Cincinnati, OH (US); Robert Wayne Glenn, Jr., Liberty Township, OH (US); Todd Ryan Thompson, Loveland, OH (US); Jazmin Veronica Torres Rivera, Liberty Township, OH (US); Sarah Elizabeth Mullen, Cincinnati, OH (US); Howard David Hutton, III, Oregonia, OH (US); Peter Herbert Koenig, Montgomery, OH (US); David Michael Eike, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/135,701

(22) Filed: Apr. 22, 2016

(65) Prior Publication Data

US 2016/0310402 A1    Oct. 27, 2016

Related U.S. Application Data

(60) Provisional application No. 62/151,601, filed on Apr. 23, 2015.

(51) Int. Cl.
| | |
|---|---|
| *A61Q 5/12* | (2006.01) |
| *A61K 8/73* | (2006.01) |
| *A61K 8/33* | (2006.01) |
| *A61K 8/42* | (2006.01) |
| *A61K 8/44* | (2006.01) |
| *A61K 8/46* | (2006.01) |
| *A61Q 5/02* | (2006.01) |
| *A61K 8/81* | (2006.01) |
| *A61K 8/04* | (2006.01) |
| *A61K 8/06* | (2006.01) |
| *A61K 8/35* | (2006.01) |
| *A61K 8/89* | (2006.01) |
| *A61Q 5/00* | (2006.01) |

(52) U.S. Cl.
CPC ............ *A61K 8/737* (2013.01); *A61K 8/046* (2013.01); *A61K 8/06* (2013.01); *A61K 8/33* (2013.01); *A61K 8/35* (2013.01); *A61K 8/42* (2013.01); *A61K 8/442* (2013.01); *A61K 8/463* (2013.01); *A61K 8/466* (2013.01); *A61K 8/8194* (2013.01); *A61K 8/89* (2013.01); *A61Q 5/006* (2013.01); *A61Q 5/02* (2013.01); *A61Q 5/12* (2013.01); *A61K 2800/49* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| | | |
|---|---|---|
| 4,329,334 A | 5/1982 | Su et al. |
| 4,867,971 A | 9/1989 | Ryan et al. |
| 5,294,644 A | 3/1994 | Login et al. |
| 5,417,965 A | 5/1995 | Janchitraponvej et al. |
| 5,776,444 A | 7/1998 | Birtwistle et al. |
| 5,816,446 A | 10/1998 | Steindorf et al. |
| 6,015,780 A | 1/2000 | Llosas Bigorra et al. |
| 6,020,303 A | 2/2000 | Cripe et al. |
| 6,046,152 A | 4/2000 | Vinson et al. |
| 6,060,443 A | 5/2000 | Cripe et al. |
| 6,087,309 A | 7/2000 | Vinson et al. |
| 6,133,222 A | 10/2000 | Vinson et al. |
| 6,162,834 A | 12/2000 | Sebillotte-Arnaud et al. |
| 6,268,431 B1 | 7/2001 | Snyder et al. |
| 6,335,312 B1 | 1/2002 | Coffindaffer et al. |
| 6,579,907 B1 | 6/2003 | Sebillotte-Arnaud et al. |
| 6,743,760 B1 | 6/2004 | Hardy et al. |
| 7,541,320 B2 | 2/2009 | Dabkowski et al. |
| 7,531,497 B2 | 5/2009 | Midha et al. |
| 7,666,825 B2 | 2/2010 | Wagner et al. |
| 8,609,600 B2 | 12/2013 | Warr et al. |
| 8,741,363 B2 | 6/2014 | Albrecht et al. |
| 8,771,765 B1 | 7/2014 | Fernandez |
| 9,186,642 B2 | 11/2015 | Dihora et al. |
| 9,308,398 B2 | 4/2016 | Hutton et al. |
| 2001/0000467 A1 | 4/2001 | Murray |
| 2001/0006621 A1 | 7/2001 | Coupe et al. |
| 2001/0016565 A1 | 8/2001 | Bodet et al. |
| 2002/0037299 A1 | 3/2002 | Turowski-Wanke et al. |
| 2003/0022799 A1 | 1/2003 | Alvarado et al. |

(Continued)

FOREIGN PATENT DOCUMENTS

| | | |
|---|---|---|
| CA | 2078375 A1 | 3/1994 |
| CN | 102697668 B | 8/2013 |
| CN | 102697670 B | 7/2014 |
| EP | 0 574 086 A2 | 12/1993 |
| EP | 1346720 A2 | 9/2003 |

(Continued)

OTHER PUBLICATIONS

PCT International Search Report and Written Opinion for PCT/US2016/028728 dated Aug. 5, 2016, 15 pages.

(Continued)

*Primary Examiner* — Jyothsna A Venkat
(74) *Attorney, Agent, or Firm* — Angela K. Haughey

(57) ABSTRACT

This invention relates to a foamable concentrated hair care composition comprising an anionic surfactant, a co-surfactant, a viscosity reducing agent, and a cationic polymer. The hair care composition may further comprise a silicone, wherein the silicone particle size is less than about 10 microns. The hair care composition has a viscosity of from about 1 to about 3,000 cps.

4 Claims, No Drawings

(56) References Cited

U.S. PATENT DOCUMENTS

| | | | |
|---|---|---|---|
| 2003/0049292 | A1 | 3/2003 | Turowski-Wanke et al. |
| 2003/0180246 | A1 | 9/2003 | Frantz |
| 2003/0185867 | A1 | 10/2003 | Kerschner et al. |
| 2003/0223951 | A1 | 12/2003 | Geary et al. |
| 2003/0228272 | A1 | 12/2003 | Amjad |
| 2004/0014879 | A1* | 1/2004 | Denzer ............... A61K 8/39 524/588 |
| 2005/0020468 | A1 | 1/2005 | Frantz et al. |
| 2006/0057075 | A1 | 3/2006 | Arkin et al. |
| 2006/0079419 | A1 | 4/2006 | Wagner et al. |
| 2006/0079420 | A1 | 4/2006 | Wagner et al. |
| 2006/0079421 | A1 | 4/2006 | Wagner et al. |
| 2006/0120982 | A1* | 6/2006 | Derici ................ A61K 8/06 424/70.12 |
| 2006/0120988 | A1 | 6/2006 | Bailey et al. |
| 2007/0154402 | A1 | 7/2007 | Trumbore |
| 2009/0029900 | A1 | 1/2009 | Cetti |
| 2009/0155383 | A1 | 6/2009 | Kitko et al. |
| 2009/0178210 | A1* | 7/2009 | Bistram .............. A61K 8/39 8/431 |
| 2009/0221463 | A1 | 9/2009 | Kitko et al. |
| 2009/0312224 | A1 | 12/2009 | Yang et al. |
| 2011/0008267 | A1 | 1/2011 | Arkin et al. |
| 2011/0165107 | A1* | 7/2011 | Derks ................. A61K 8/85 424/70.11 |
| 2011/0319790 | A1 | 12/2011 | Kost et al. |
| 2012/0100091 | A1* | 4/2012 | Hata .................. A61K 8/44 424/70.19 |
| 2012/0316095 | A1 | 12/2012 | Wei et al. |
| 2013/0280202 | A1 | 10/2013 | Stella et al. |
| 2014/0039066 | A1 | 2/2014 | Grimadell et al. |
| 2014/0237732 | A1 | 8/2014 | Zuedel Fernandes et al. |
| 2014/0309154 | A1 | 10/2014 | Carter et al. |
| 2014/0348886 | A1 | 11/2014 | Johnson et al. |
| 2015/0021496 | A1 | 1/2015 | Shabbir |
| 2015/0098921 | A1 | 4/2015 | Franzke et al. |
| 2016/0113849 | A1 | 4/2016 | Grimadell et al. |
| 2016/0193125 | A1 | 7/2016 | Jones et al. |
| 2016/0310369 | A1 | 10/2016 | Thompson et al. |
| 2016/0310370 | A1 | 10/2016 | Zhao et al. |
| 2016/0310386 | A1 | 10/2016 | Smith, III et al. |
| 2016/0310388 | A1 | 10/2016 | Smith, III et al. |
| 2016/0310389 | A1 | 10/2016 | Thompson et al. |
| 2016/0310390 | A1 | 10/2016 | Smith, III et al. |
| 2016/0310391 | A1 | 10/2016 | Smith, III et al. |
| 2016/0310393 | A1 | 10/2016 | Chang et al. |
| 2016/0310402 | A1 | 10/2016 | Zhao et al. |
| 2016/0354300 | A1 | 12/2016 | Thompson et al. |
| 2017/0209359 | A1 | 7/2017 | Zhao et al. |
| 2017/0304172 | A1 | 10/2017 | Chang et al. |

FOREIGN PATENT DOCUMENTS

| | | |
|---|---|---|
| JP | 3069802 B2 | 7/2000 |
| WO | WO2005023975 A1 | 3/2005 |
| WO | WO 2012/055587 A1 | 5/2012 |
| WO | WO 2012/084970 A1 | 6/2012 |
| WO | WO 2013/010706 A2 | 1/2013 |

OTHER PUBLICATIONS

PCT International Search Report and Written Opinion for PCT/US2016/028729 dated Jun. 15, 2016, 11 pages.
PCT International Search Report and Written Opinion for PCT/US2016/028730 dated Aug. 5, 2016, 16 pages.
PCT International Search Report and Written Opinion for PCT/US2016/058123 dated Dec. 21, 2016, 17 pages.
PCT International Search Report and Written Opinion for PCT/US2016/028742 dated Jul. 18, 2016.
PCT International Search Report and Written Opinion for PCT/US2016/028735 dated Jul. 25, 2016.
PCT International Search Report and Written Opinion for PCT/US2016/028736 dated Jul. 25, 2016.
U.S. Appl. No. 15/788,938, filed Oct. 20, 2017, Torres Rivera et al.
U.S. Appl. No. 15/788,949, filed Oct. 20, 2017, Torres Rivera et al.
U.S. Appl. No. 15/788,957, filed Oct. 20, 2017, Torres Rivera et al.
U.S. Appl. No. 15/788,998, filed Oct. 20, 2017, Torres Rivera et al.
U.S. Appl. No. 15/789,010, filed Oct. 20, 2017, Torres Rivera et al.
U.S. Appl. No. 15/789,020, filed Oct. 20, 2017, Renock et al.
U.S. Appl. No. 15/789,030, filed Oct. 20, 2017, Renock et al.
U.S. Appl. No. 15/789,038, filed Oct. 20, 2017, Thompson et al.
U.S. Appl. No. 15/789,044, filed Oct. 20, 2017, Johnson et al.
U.S. Appl. No. 15/789,081, filed Oct. 20, 2017, Glenn, Jr. et al.
U.S. Appl. No. 15/789,172, filed Oct. 20, 2017, Zhao et al.
U.S. Appl. No. 15/789,188, filed Oct. 20, 2017, Zhao et al.
U.S. Appl. No. 15/789,208, filed Oct. 20, 2017, Zhao et al.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.
All Final and Non-Final Office Actions for U.S. Appl. No. 15/299,860.
All Final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.
All Final and Non-Final Office Actions for U.S. Appl. No. 15/789,172.
All Final and Non-Final Office Actions for U.S. Appl. No. 15/789,188.
All Final and Non-Final Office Actions for U.S. Appl. No. 15/789,208.

* cited by examiner

LOW VISCOSITY HAIR CARE COMPOSITION

FIELD OF THE INVENTION

The present invention relates to a hair care composition having low viscosity and method of manufacturing a low viscosity hair care composition.

BACKGROUND OF THE INVENTION

Described herein is a hair care composition that enables new product opportunities and consumer benefits by addressing the current disadvantages associated with hair care compositions. It has been found that stable concentrated and low viscosity hair care compositions can be delivered to the hair in various forms including a foamed form. Delivery of cleansing composition in the form of foam represents an attractive consumer concept. Typically, high surfactant liquid cleansing composition exhibit high viscosity, which makes it difficult to deliver via a pump foam dispenser, a squeeze foam dispenser or an aerosol foam dispenser. Therefore, delivery as a foam is facilitated by low viscosity concentrated liquid compositions.

Hair care compositions comprising (a) above about 20% total surfactants, wherein the surfactants comprises of (i) anionic surfactants (ii) amphoteric and/or zwitterionic surfactants, (iii) optionally nonionic surfactants; and (b) viscosity reducing agents provide stable compositions having viscosity below about 3000 centipoise. Viscosity reducing agents can include: Class A materials, Class B materials, water miscible glycols and mixtures thereof. The composition comprises 1% or more zwitterionic molecules which possess a hydroxyl group.

In order to deliver consumer acceptable wet conditioning feel, the hair care composition also comprises a cationic polymer. The hair care composition is able to deliver low viscosity concentrated liquid cleansing compositions even in the presence of cationic polymers which typically raise liquid viscosity. Cationic polymers suitable for use include those having a weight average molecular weight less than about 1,000,000 g/mol.

Additionally, the hair care composition may further comprise one of more benefit agent including, but not limited to, silicone materials to enhance the consumer desirable wet and dry conditioning feel. Suitable silicone materials include those silicone emulsions having a particle size of less than about 10 micrometers. Silicones less suitable for use include non-emulsified silicones and/or large particle silicone emulsions which may result in a phase unstable composition.

SUMMARY OF THE INVENTION

The invention relates to a hair care composition comprising greater than about 20% by weight of a surfactant system comprising: from about 10% to about 40% of one or more anionic surfactants; from about 1% to about 15% of one or more co-surfactants selected from the group consisting of amphoteric, zwitterionic, nonionic and mixtures thereof; wherein about 1% or more are zwitterionic surfactants which possess a hydroxyl group in their molecular structure; from about 0.1% to about 35% by weight of one or more viscosity reducing agents; from about 0.05% to about 1% by weight of one or more cationic polymers with a weight average molecular weight of less than about 1,000,000 g/mol; wherein the hair care composition has a viscosity of from about 1 centipoise to about 3,000 centipoise.

The hair care composition described above wherein the viscosity reducing agent is selected from the group consisting of Class A materials, Class B materials, water miscible solvents and mixtures thereof. The viscosity reducing agent can be selected from water miscible solvents and wherein the viscosity reducing agent can be included at from about 0.1% to about 35% by weight, alternatively at from about 2% to about 30% by weight, alternatively at from about 4% to about 25% by weight. The hair care composition described above can include glycol as one of the water miscible solvents. The glycol can be selected from propylene glycol, dipropylene glycol, tripropylene glycol, and glycerin. They glycol selected can be dipropylene glycol.

The hair care composition described above can include a anionic surfactant selected from the group consisting of sodium laureth sulfate (where R is $C_{12}$ alkyl and $M^+$ is $Na^+$, n=1-3), ammonium laureth sulfate (where R is $C_{12}$ alkyl, $M^+$ is $NH_3^+$, n=1-3), sodium trideceth sulfate (where R is $C_{13}$ alkyl, $M^+$ is $Na^+$, and n=1-4); and mixtures thereof. The hair care composition of can be dispensed as a foam. The foam can have a density of from about 0.025 $g/cm^3$ to about 0.30 $g/cm^3$; alternatively from about 0.05 $g/cm^3$ to about 0.20 $g/cm^3$; alternatively from about 0.075 $g/cm^3$ to about 0.15 $g/cm^3$. The foam can be dispensed as an aerosol foam and comprise from about 1% to about 10% by weight of a propellant.

The hair care composition as described above can have a co-surfactants selected from the group consisting of cocamidopropyl betaine, lauramidopropyl betaine, cocamide monoethanolamine, lauryl hydroxysultaine, sodium lauroamphoacetate, and mixtures thereof. The lauramidopropyl betaine, lauryl hydroxysultaine and sodium lauroamphoacetate can have a C12 chain length of from about 80% to about 100%; alternatively the lauramidopropyl betaine, lauryl hydroxysultaine and sodium lauroamphoacetate have a C12 chain length of from about 85% to about 100%; alternatively the lauramidopropyl betaine, lauryl hydroxysultaine and sodium lauroamphoacetate can have a C12 chain length of from about 90% to about 100%; alternatively the lauramidopropyl betaine, lauryl hydroxysultaine and sodium lauroamphoacetate can have a C12 chain length of from about 95% to about 100%; alternatively the lauramidopropyl betaine, lauryl hydroxysultaine and sodium lauroamphoacetate have a C12 chain length of from about 97% to about 99%.

The hair care composition described above wherein the anionic surfactant is sodium laureth sulfate with an average of one mole ethoxylate.

The hair care composition described above further comprising from 0.01 to about 4% of one or more silicone emulsion, wherein said silicone has a particle size less than about 10 micrometers. The silicone emulsion can be selected from the group consisting of dimethiconol/dimethicone, silicone quaternium-22, silicone quaternium-17, silicone quaternium-80 micro-emulsion, and mixtures thereof.

The hair care composition described above, wherein the cationic polymers are selected from the group consisting of guar hydroxypropyl trimonium chloride; Polyquaternium-10, and Polyquaterinum-6. The cationic polymer can have a weight average molecular weight of less than about 1.0 million g/mol and greater than about 50,000 g/mol, alternatively less than about 900,000 g/mol, alternatively less than about 800,000 g/mol.

The hair care composition described above wherein the viscosity is from about 1 to about 2,500 cps, alternatively from about 1 to about 2,000 cps.

DETAILED DESCRIPTION OF THE INVENTION

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

As used herein, "personal care compositions" includes products such as shampoos, shower gels, liquid hand cleansers, hair colorants, facial cleansers, and other surfactant-based liquid compositions As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the hair care composition.

Hair Care Composition

The hair care composition comprises i) above about 20% by weight of a surfactant mixture of which at least 1% or more are zwitterionic surfactants which possess a hydroxyl group along with both positive and negative charges within the same molecule, ii) viscosity reducing agents (at a concentration above about 4%) ii) a cationic polymer and iv) may further comprise a silicone and optional ingredients. The hair care composition can be delivered in the form of a foam.

Delivery of cleansing composition in the form of foam represents an attractive consumer concept. Having a low density foam allows for a high concentration of surfactant to deliver sufficient amount of detersive surfactant for each use. Typically, high surfactant liquid cleansing composition exhibits high viscosity, which makes it difficult to deliver with a typical pump foam dispenser or a typical aerosol foam dispenser. Therefore, delivery of a shampoo via foam requires very low viscosity concentrated liquid cleansing compositions. The resulting composition has a viscosity below about 3000 cps.

A. Detersive Surfactant

The hair care composition may comprise greater than about 20% by weight of a surfactant system which provides cleaning performance to the composition. The surfactant system comprises an anionic surfactant and/or a combination of anionic surfactants, with a co-surfactant selected from the group consisting of amphoteric, zwitterionic, nonionic and mixtures thereof. The surfactant system may comprise at 1% or more of the surfactants are zwitterionic surfactants which possess a hydroxyl group in their molecular structure. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

The hair care composition may comprise from about 10% to about 40%, from about 15% to about 36%, from about 18% to about 32%, and/or from about 20% to about 28% by weight of one or more anionic surfactants.

Suitable anionic detersive surfactant components for use in the composition herein include those which are known for use in hair care or other personal care shampoo compositions. The anionic detersive surfactant may be a combination of sodium lauryl sulfate and sodium laureth-n sulfate. Alternatively, the anionic detersive surfactant can be sodium laureth sulfate with an average of one mole ethoxylate. The concentration of the anionic surfactant component in the composition should be sufficient to provide the desired cleaning and lather performance Anionic surfactants suitable for use herein include alkyl sulfates and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

TABLE 1

Examples of Typical Alkyl Sulfates and Alky Ether Sulfates

| Surfactant | Supplier | Activity | SLS | SLE1S | SLE2S | SLE3S | SLE > 3S |
|---|---|---|---|---|---|---|---|
| Sodium Lauryl Sulfate | Stepan STEOL SLS | 29% by weight | 100 | 0 | 0 | 0 | 0 |
| Sodium Laureth-1 Sulfate | Stepan STEOL SLES-1 | 26% by weight | 45.5 | 26.3 | 11.8 | 0.07 | 16.33 |
| Sodium Laureth-3 Sulfate | Stepan STEOL SLES-3 | 28% by weight | 18 | 16.7 | 12.6 | 12.4 | 40.30 |

The composition of the present invention can also include anionic surfactants selected from the group consisting of:
a) $R_1O(CH_2CHR_{30})_y SO_3M$;
b) $CH_3(CH_2)_zCHR_2CH_2O(CH_2CHR_{30})_z SO_3M$; and
c) mixtures thereof, where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is to 7, the average value of y is about 1 when y is not zero (0), and M is a monovalent or divalent, positively-charged cation.

The composition can also include anionic alkyl sulfates and alkyl ether sulfate surfactants having branched alkyl chains which are synthesized from C8 to C18 branched alcohols which may be selected from: Guerbet alcohols, aldol condensation derived alcohols, oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISO-FOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfates and sodium trideceth-3 sulfates. The composition can also include sodium tridecyl sulfate.

Some non-limiting examples of surfactants are:
Alkyl Sulfates

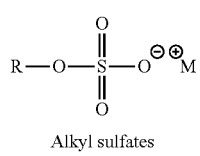

Alkyl sulfates where R is $C_8$-$C_{24}$ alkyl (linear or branched, saturated or unsaturated) and M+ is monovalent cation. Examples include Sodium lauryl sulfate (where R is $C_{12}$ alkyl and M+ is Na+), ammonium lauryl sulfate (where R is $C_{12}$ alkyl and M+ is $NH_3^+$), and sodium coco-sulfate (where R is coconut alkyl and M+ is Na+);

Alkyl Ether Sulfates

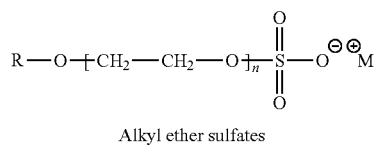

Alkyl ether sulfates where R is $C_8$-$C_{24}$ alkyl (linear or branched, saturated or unsaturated) or mixtures thereof, n=1-12, and M+ is monovalent cation. Examples include sodium laureth sulfate (where R is $C_{12}$ alkyl and M+ is Na+, n=1-3), ammonium laureth sulfate (where R is $C_{12}$ alkyl, M+ is $NH_3^+$, n=1-3), and Sodium trideceth sulfate (where R is $C_{13}$ alkyl, M+ is Na+, and n=1-4);

Some non-limiting examples of sulfonate surfactants are:
Alkyl Glyceryl Ether Sulforiates:

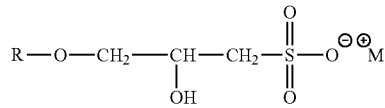

where R=$C_8$-$C_{24}$ alkyl (linear or branched, saturated or unsaturated) or mixtures thereof and M+=monovalent cation, such as Sodium Cocoglyceryl Ether Sulfonate (R=coco alkyl, M+=Na+);

Alpha olefin sulfonates prepared by sulfonation of long chain alpha olefins. Alpha olefin sulfonates consist of mixtures of alkene sulfonates,

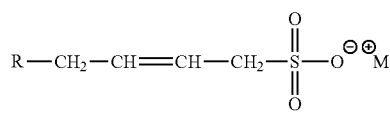

where R=$C_8$-$C_{18}$ alkyl or mixtures thereof and M+=monovalent cation; Hydroxyalkyl sulfonates,

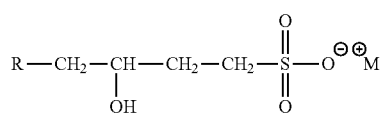

where R=$C_4$-$C_{18}$ alkyl or mixtures thereof and M+=monovalent cation. Examples include Sodium C12-14 Olefin Sulfonate (R=$C_8$-$C_{10}$ alkyl, M+=Na+) and Sodium C 14-16 Olefin Sulfonate (R=$C_{10}$-$C_{12}$ alkyl, M+=Na+).

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

The hair care composition comprises from about 1% to about 15%, from about 2% to about 14%, from about 3% to about 13% by weight of one or more co-surfactants selected from the group consisting of amphoteric surfactant, zwitterionic surfactant, non-ionic surfactant and mixtures thereof. However, of the co-surfactants, at least about 1% are zwitterionic molecules which possess a hydroxyl group along with positive and negative charges within the same molecule.

The suitable zwitterionic co-surfactants possess a hydroxyl group in their molecular structure are:

Alkyl hydroxysultains

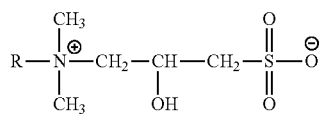

Alkyl hydroxysultaines where R is alkyl group with $C_8$ to $C_{24}$ carbon chain (saturated or unsaturated) or mixture thereof. Examples include lauryl hydroxysultaine (where R is lauryl; $C_{12}H_{25}$) and coco-hydroxysultaine (where R is coco alkyl).

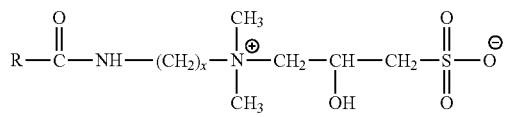

where RCO=$C_6$-$C_{24}$ acyl (saturated or unsaturated) or mixtures thereof. Examples include Cocamidopropyl Hydroxysultaine (RCO=coco acyl, x=3), Lauramidopropyl Hydroxysultaine (RCO=lauroyl, and x=3), Myristamidopropyl Hydroxysultaine (RCO=myristoyl, and x=3), and Oleamidopropyl Hydroxysultaine (RCO=oleoyl, and x=3).

Alkyl amphoacetates

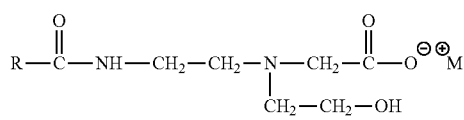

Alkyl amphoacetates where R is alkyl group with $C_6$ to $C_{24}$ carbon chain (saturated or unsaturated) or mixtures thereof and $M^+$ is monovalent cation. Examples include sodium lauroamphoacetate (where R is lauryl and $M^+$ is $Na^+$) and sodium cocoamphoacetate (where R is coco and $M^+$ is $Na^+$).

Alkyl amphopropionates

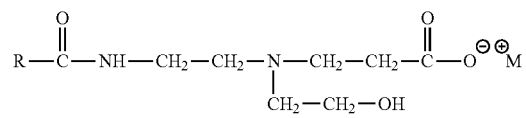

where RCO=$C_6$-$C_{24}$ acyl (saturated or unsaturated) or mixtures thereof and $M^+$=monovalent cation. Examples include Sodium Lauroamphopropionate (RCO=lauroyl and $M^+$=$Na^+$) and Sodium Cocoamphopropionate (RCO=coco acyl and $M^+$=$Na^+$).

Alkyl amphohydroxypropylsulfonates:

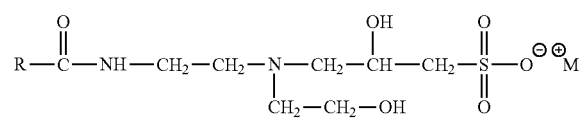

where RCO=$C_6$-$C_{24}$ acyl (saturated or unsaturated) or mixtures thereof and $M^+$=monovalent cation. Examples include Sodium Lauroamphohydroxypropylsulfonate (RCO=lauroyl and $M^+$=$Na^4$) and Sodium Cocoamphohydroxypropylsulfonate (RCO=coco acyl and $M^+$=$Na^+$).

Alkyl posphobetaines:

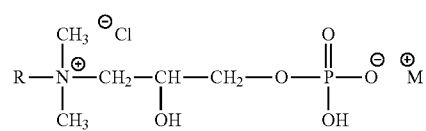

where R=$C_6$-$C_{24}$ alkyl (saturated or unsaturated) or mixtures thereof and $M^+$=monovalent cation, such as Sodium Coco PG-Dimonium Chloride Phosphate, where R=coco alkyl and $M^+$=$Na^+$ Amphohydroxyalkylphosphates of the formula:

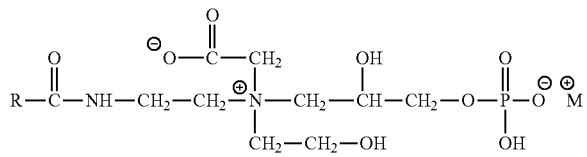

Suitable amphoteric or zwitterionic surfactants for use in the hair care composition herein include those which are known for use in shampoo or other hair care cleansing. Non limiting examples of suitable zwitterionic or amphoteric surfactants are described in U.S. Pat. Nos. 5,104,646 and 5,106,609, which are incorporated herein by reference in their entirety.

Suitable zwitterionic surfactants can be selected from the group consisting of lauryl hydroxysultaine (where R is lauryl. $C_{12}H_{25}$) and coco-hydroxysultaine (where R is coco alkyl) and mixtures thereof. Suitable hydroxyl group containing zwitterionic surfactants can be selected from the group consisting of sodium lauroamphoacetate (where R is lauryl and $M^+$ is $Na^+$), sodium cocoamphoacetate (where R is coco acyl and M+ is Na+), and mixtures thereof. Alternatively the hydroxyl group containing zwitterionic surfactants can be selected from the group consisting of Sodium Lauroamphopropionate (RCO=lauroyl and M+=Na+) and Sodium Cocoamphopropionate (RCO=coco acyl and M+=Na+). Alternatively, the hydroxyl group containing zwitterionic surfactants can be selected from the group consisting of Sodium Coco PG-Dimonium Chloride Phosphate, where R=coco alkyl and M+=Na+. Alternatively, the hydroxyl group containing zwitterionic surfactants can be selected from Sodium Lauroampho PG-Acetate Phosphate (RCO=lauroyl and M+=Na+).

Amphoteric co-surfactanLs suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The amphoteric co-surfactant can be a surfactant according to the following structure:

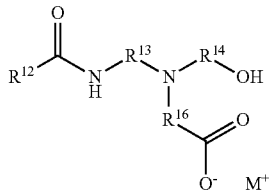

wherein R12 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R13, R14, and R15 are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine. The amphoteric surfactant may be selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

The composition may comprises a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. A suitable zwitterionic surfactant is lauryl hydroxysultaine. The zwitterionic surfactant can be selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be a zwitterionic surfactant, wherein the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof.

Non limiting examples of other anionic, zwitterionic, amphoteric, and non-ionic additional surfactants suitable for use in the hair care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable amphoteric/zwitterionic or nonionic co-surfactants can be selected from the group consisting of:

Alkyl Betaines

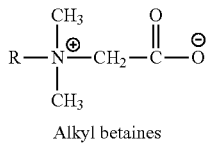

Alkyl betaines where R is $C_8$-$C_{24}$ alkyl (saturated or unsaturated) or mixtures thereof. Examples include coco-betaine (where R is coco alkyl), lauryl betaine (where R is lauryl, $C_{12}H_{25}$), and oleyl betaine (where R is oleyl, $C_{18}H_{35}$), Alkanolamide:

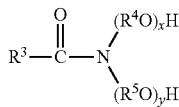

wherein: $R^3$ is $C_5$-$C_{24}$ saturated or unsaturated, straight chain or branched aliphatic group, $R^4$ and $R^5$ are the same or different, $C_2$-$C_4$ straight chain or branched aliphatic groups, x is an integer from 0 to 10, y is an integer from 1 to 10, and the sum of x and y is less than or equal to 10, Alkyl hydroxysultains

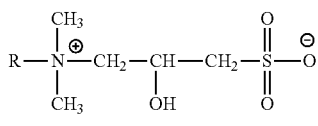

Alkyl hydroxysultaines where R is $C_8$-$C_{24}$ alkyl (saturated or unsaturated) or mixture thereof. Examples include lauryl hydroxysultaine (where R is lauryl, $C_{12}H_{25}$) and coco-hydroxysultaine (where R is coco alkyl), Alkyl amphoacetates

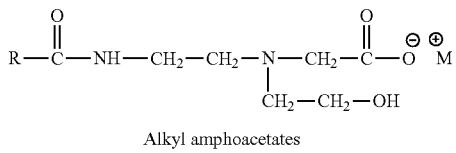

Alkyl amphoacetates where R is $C_6$-$C_{24}$ alkyl (saturated or unsaturated) or mixtures thereof and $M^+$ is monovalent cation. Examples include sodium lauroamphoacetate (where R is lauryl and $M^+$ is $Na^+$), sodium cocoamphoacetate (where R is coco acyl and $M^+$ is $Na^+$) and mixtures thereof.

Suitable co-surfactants can be selected from the group consisting of cocamidopropyl betaine, lauramidopropyl betaine, cocamide monoethanolamine, lauryl hydroxysultaine and sodium lauroamphoacetate, and mixtures thereof.

The co-surfactant can be selected from amphoteric or zwitterionic surfactants synthesized from lauric acid including, but not limited to, lauramidopropyl betaine, lauryl Hydroxysultaine, and sodium lauroamphoacetate and having a chain length distribution wherein the C12 chain length averages from about 80% to about 100%, alternatively from about 85% to about 100%, alternatively from about 90% to about 100%, alternatively from about 95% to about 100%, and alternatively from about 97% to about 100% of the total molecular chain length distribution.

The hair care composition can comprise from about 2% to about 14%, alternatively from about 3% to about 12% by weight of the hair care composition, of a zwitterionic surfactant which has a hydroxyl group in the molecular structure.

B. Cationic Polymers

The hair care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer, may including but is not limited to a cationic guar polymer, having a molecular weight of less than 1.0 million g/mol, or from about 10 thousand to about 1 million g/mol, or from about 25 thousand to about 1 million g/mol, or from about 50 thousand to about 1 million g/mol, or from about 100 thousand to about 1 million g/mol. The cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.7 meq/g.

The cationic guar polymer may have a weight average molecular weight of less than about 1.0 million g/mol, and a charge density of from about 0.1 meq/g to about 2.5 meq/g. The cationic guar polymer may have a weight average molecular weight of less than 950 thousand g/mol, or from about 10 thousand to about 900 thousand g/mol, or from about 25 thousand to about 900 thousand g/mol, or from about 50 thousand to about 900 thousand g/mol, or from about 100 thousand to about 900 thousand g/mol. from about 150 thousand to about 800 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The hair care composition can comprise from about 0.05% to less than about 1%, from about 0.05% to about 0.9%, from about 0.1% to about 0.8%, or from about 0.2% to about 0.7% of cationic polymer (a), by total weight of the composition.

The cationic guar polymer may be formed from quaternary ammonium compounds. The quaternary ammonium compounds for forming the cationic guar polymer can conform to the general formula 1:

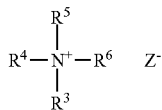

wherein where $R^3$, $R^4$ and $R^5$ are methyl or ethyl groups; $R^6$ is either an epoxyalkyl group of the general formula 2:

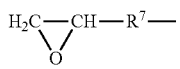

or $R^6$ is a halohydrin group of the general formula 3:

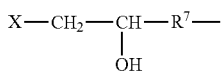

wherein $R^7$ is a $C_1$ to $C_3$ alkylene; X is chlorine or bromine, and Z is an anion such as Cl—, Br—, I— or $HSO_4$—.

The cationic guar polymer can conforms to the general formula 4:

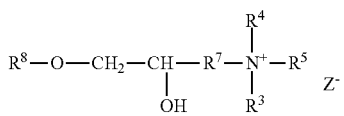

wherein $R^8$ is guar gum; and wherein $R^4$, $R^5$, $R^6$ and $R^7$ are as defined above; and wherein Z is a halogen. The cationic guar polymer can conform to Formula 5:

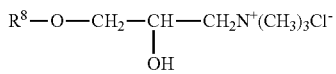

Suitable cationic guar polymers include cationic guar gum derivatives, such as guar hydroxypropyltrimonium chloride. The cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.1 meq/g and a molecular weight of about 500,000 g/mol is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Rhodia; N-Hance 3269 and N-Hance 3270, which has a charge density of about 0.7 meq/g and a molecular weight of about 425,000 g/mol and is available from ASIAquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.7 meq/g and M. W.t of about 800,000 both available from ASI.

The hair care compositions may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives suitable for use can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The non-guar galactomannan polymer derivatives can have a M. Wt. from about 1,000 to about 1,000,000, and/or form about 5,000 to about 900,000.

The hair care compositions of the can also include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

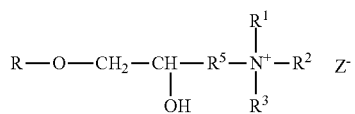

wherein R is the gum. The cationic galactomannan derivative can be a gum hydroxypropyltrimethylammonium chloride, which can be more specifically represented by the general formula 7:

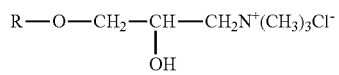

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 50,000 g/mol to about 1,000,000 g/mol, and/or from about 100,000 g/mol to about 900,000 g/mol and a cationic charge density from about 1 meq/g to about 5 meq/g, and/or from 2 meq/g to about 4 meq/g and can also be derived from a *cassia* plant.

The hair care compositions can comprise at least about 0.05% of a galactomannan polymer derivative by weight of the composition, alternatively from about 0.05% to about 2%, by weight of the composition, of a galactomannan polymer derivative.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The hair care compositions can comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the hair care compositions can have a molecular weight about 50,000 g/mol to about 1,000,000 g/mol and/or from about 100,000 g/mol to about 1,000,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:
(i) an acrylamide monomer of the following Formula AM:

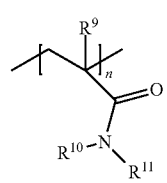

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

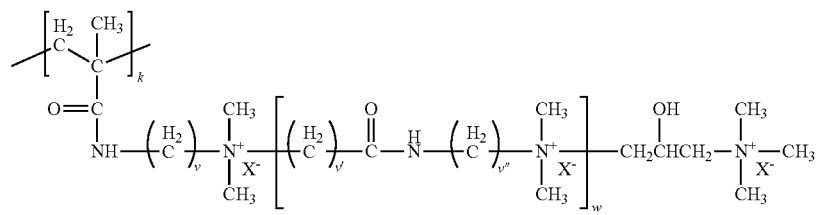

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

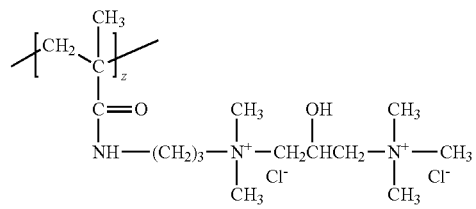

The above structure may be referred to as diquat. Alternatively, the cationic monomer can conform to Formula CM and wherein v and v" are each 3, v'=1, w=1, y=1 and $X^-$ is $Cl^-$, such as:

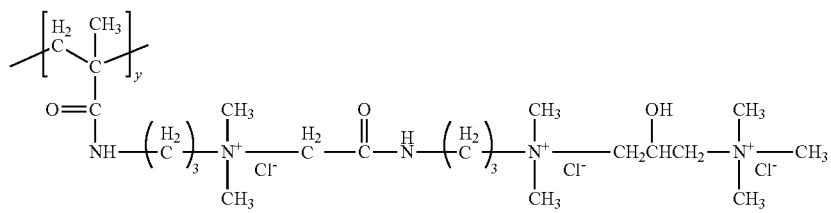

The above structure may be referred to as triquat.

Suitable acrylamide monomer include, but are not limited to, either acrylamide or methacrylamide.

In an alternative, the cationic copolymer can be an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. The cationized esters of the (meth)acrylic acid containing a quaternized N atom can be quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters can be the (meth)acrylic acid containing a quaternized N atom is dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 10 thousand g/mol to about 1 million g/mol, or from about 25 thousand g/mol to about 1 million g/mol, or from about 50 thousand g/mol to about 1 million g/mol, or from about 100 thousand g/mol to about 1.0 million g/mol, or from about 150 thousand g/mol to about 1.0 million g/mol.

(a) Cationic Synthetic Polymers

The hair care composition can comprise a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

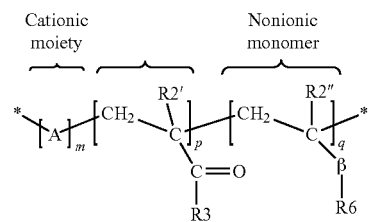

$m \geq 1$
$p = 0$ or $\geq 1$
$q = 0$ or $\geq 1$
$m \geq p$ where A, may be one or more of the following cationic moieties:

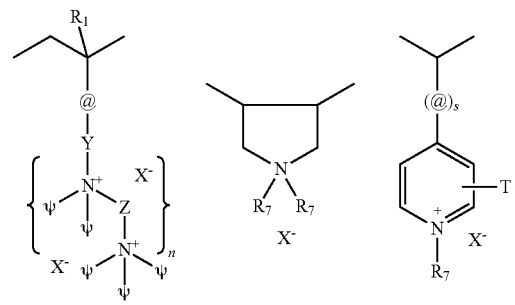

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or z 1;
where T and R7=C1-C22 alkyl; and
where X—=halogen, hydroxide, alkoxide, sulfate or alkylsulfate.

Where the monomer bearing a negative charge is defined by R2'=H, C1-C4 linear or branched alkyl and R3 as:

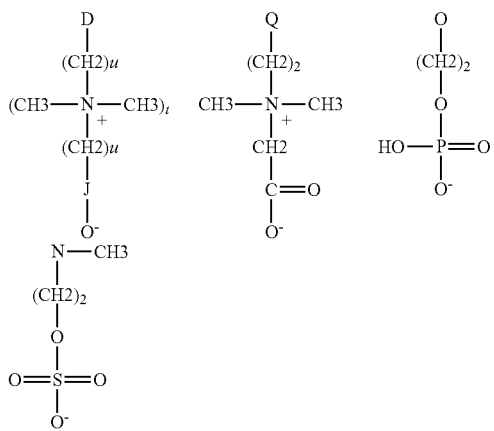

where D=O, N, or S;
where Q=NH$_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics.

Non limiting examples of such counterions include halides (e.g., chlorine, fluorine, bromine, iodine), sulfate and methylsulfate.

The concentration of the cationic polymers ranges about 0.025% to about 5%, from about 0.1% to about 3%, and/or from about 0.2% to about 1%, by weight of the hair care composition.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

C. Viscosity Reducing Agents

The hair care composition described herein may comprise from about 0.1% to about 35%, alternatively from about 0.5% to about 30%, and alternatively from about 1% to about 25% of a viscosity reducing agent, by weight of the hair care composition. Non-limiting examples of suitable viscosity reducing agents include Class A materials, Class B materials, water miscible solvents and mixtures thereof.

The hair care composition described herein may comprise from about 1% to about 10%, alternatively from about 3.25% to about 9%, alternatively from about 3.5% to about 8%, and alternatively from about 4% to about 7% of one or more viscosity reducing agents, by weight of the hair care composition.

The hair care composition described herein may have a liquid phase viscosity of from about 1 centipoise to about 3,000 centipoise, alternatively from about 1 centipoise to about 2,500 centipoise, alternatively from about 1 centipoise to about 2,000 centipoise, and alternatively from about 5 centipoise to about 1,500 centipoise. The hair composition viscosity values may be measured using a TA Instruments AR-G2 Rheometer with a concentric cylinder attachment at a shear rate of 100 reciprocal seconds at 25° C.

The hair care composition described herein may have a viscosity of from about 10 cSt to about 500 cSt, alternatively from about 15 cSt to about 400 cSt, alternatively from about 20 cSt to about 300 cSt, alternatively from about 25 cSt to about 250 cSt, and alternatively from about 30 cSt to about 250 cSt.

1. Class A Viscosity Reducing Agents

The Class A viscosity reducing agents may have a partition dispersion coefficient of from about −3.1 to about −0.7, alternatively from about −3 to about −0.85, and alternatively from about −2.92 to about −0.92. The Class A viscosity reducing agents may have a partition dispersion coefficient of from about −3 to about −1.9, alternatively from about −2.9 to about −2, wherein the one or more viscosity reducing agents has at least 2 polar groups, or has 1 polar group and less than 5 acyclic $sp^3$ hybridized carbon atoms that are connected to each other in a contiguous group. The Class A viscosity reducing agents may have a partition dispersion coefficient of from about −3 to about −1.9, alternatively from about −2.9 to about −2, wherein the one or more viscosity reducing agents has 2 to 4 polar groups, or has 1 polar group and 1 to 3 acyclic $sp^3$ hybridized carbon atoms that are connected to each other in a contiguous group. The Class A viscosity reducing agents may have a partition dispersion coefficient of from about −3 to about −1, alternatively from about −2.9 to about −2, wherein the one or more viscosity reducing agents has 2 to 4 polar groups, or has 1 polar group and 2 acyclic $sp^3$ hybridized carbon atoms that are connected to each other in a contiguous group. The Class A viscosity reducing agents may provide unexpected viscosity reduction when used in the hair care composition described herein.

The partition dispersion coefficient (PDC) is defined by the following equation:

$$PDC = \log P - 0.3001*(\delta D)2 + 10.362*\delta D - 93.251$$

wherein log P is the octanol water partitioning coefficient as computed by the Consensus algorithm implemented in ACD/Percepta version 14.02 by Advanced Chemistry Development, Inc. (ACD/Labs, Toronto, Canada), and wherein $\delta D$ is the Hansen solubility dispersion parameter in $(MPa)$ ½ computed using Steven Abbott and Hiroshi Yamamoto's "HSPIP—Hansen Solubility Parameters in Practice" program, 4th Edition, version 4.1.07.

The viscosity reducing agents may be organic compounds comprising 1 polar group, alternatively at least 1 polar group, alternatively 2 to 4 polar groups, and alternative alternatively at least 2 polar groups. The polar groups may be selected from the group consisting of alcohols, aldehydes, esters, lactones, coumarins, ethers, ketones, phenol, phenyl, oxides, alkenyl, alkynyl, and combinations thereof. The viscosity reducing agents may have a molecular weight of between 100 daltons and 300 daltons, alternatively from about 125 daltons to about 300 daltons. Additionally, the viscosity reducing agents may have a water solubility at between 23 and 25 degrees Celsius of from about 900 to 50,000 mg/L.

The viscosity reducing agents may be selected from the group consisting of raspberry ketone, triethyl citrate, 5-methyl-3-heptanone oxime, hydroxycitronellal, camphor gum, 2-isopropyl-5-methyl-2-hexenal, eucalyptol, 1,1-dimethoxyoctane, isobutyl hexanoate, dihyro iso jasmonate, and combinations thereof. Alternatively, the viscosity reducing agents may be selected from the group consisting of raspberry ketone, triethyl citrate, hydroxycitronellal, camphor gum, and combinations thereof. Alternatively, the viscosity reducing agent may be selected from the group consisting of raspberry ketone, triethyl citrate, hydroxycitronellal, and combinations thereof.

2. Class B Viscosity Reducing Agents

The Class B viscosity reducing agents may have a partition dispersion coefficient of from about 0.05 to about 5.1, alternatively from about 0.08 to about 4.5, alternatively from about 0.09 to about 4.4, alternatively from about 0.05 to about 2.0, alternatively from about 0.08 to about 1.8, alternatively from about 0.09 to about 1.7, and alternatively from about 0.095 to about 1.68. The Class B viscosity reducing agents may provide unexpected viscosity reduction when used in the hair care composition described herein.

The partition dispersion coefficient (PDC) is defined by the following equation:

$$PDC = \log P - 0.3001*(\delta D)^2 + 10.362*\delta D - 93.251$$

wherein log P is the octanol water partitioning coefficient as computed by the Consensus algorithm implemented in ACD/Percepta version 14.02 by Advanced Chemistry Development, Inc. (ACD/Labs, Toronto, Canada), and wherein δD is the Hansen solubility dispersion parameter in $(MPa)^{1/2}$ computed using Steven Abbott and Hiroshi Yamamoto's "HSPIP—Hansen Solubility Parameters in Practice" program, $4^{th}$ Edition, version 4.1.07.

The viscosity reducing agents may be organic compounds comprising 1 polar group, alternatively at least 1 polar group, alternatively 2 to 4 polar groups, and alternative alternatively at least 2 polar groups. The polar groups may be selected from the group consisting of alcohols, aldehydes, esters, lactones, coumarins, ethers, ketones, phenol, phenyl, oxides, alkenyl, alkynyl, and combinations thereof. The viscosity reducing agents may have a molecular weight of between 100 daltons and 300 daltons, alternatively from about 125 daltons to about 300 daltons. Additionally, the viscosity reducing agents may have a water solubility at between 23 and 25 degrees Celsius of from about 10 to 900 mg/L.

The Class B viscosity reducing agents may be selected from the group consisting of veloutone, isoamyl salicylate, gamma-terpinene, linalyl iso butyrate, alpha-terpinene, limonene, dipentene, geranyl phenyl acetate, iso propyl myristate, hexadecane, and combinations thereof. Alternatively, the Class B viscosity reducing agents may be selected from the group consisting of veloutone, gamma-terpinene, linalyl iso butyrate, alpha-terpinene, limonene, dipentene, geranyl phenyl acetate, iso propyl myristate, hexadecane, and combinations thereof. Alternatively, the Class B viscosity reducing agents may be selected from the group consisting of veloutone, isoamyl salicylate, gamma-terpinene, linalyl iso butyrate, alpha-terpinene, limonene, dipentene, geranyl phenyl acetate, and combinations thereof.

3. Water Miscible Solvents

The compositions can include water miscible glycols and other diols. Non-limiting examples include dipropylene glycol, tripropylene glycol, diethylene glycol, ethylene glycol, propylene glycol, glycerin, 1,3-propane diol, 2,2-propanediol, 1,2-butanediol, 1,3-butanediol, 1,4-butanediol, 2,3-butanediol, 2-methyl-2,4-pentanediol, and mixtures thereof. The hair care composition may comprise two or more water miscible solvents, wherein at least one of the solvents is dipropylene glycol.

D. Propellant

The hair care composition described herein may comprise from about from about 1% to about 10% propellant, alternatively from about 2% to about 8% propellant, alternatively from about 2.5% to about 7% propellant, and alternatively from about 3% to about 6% propellant by weight of the hair care composition.

The propellant may comprise one or more volatile materials, which in a gaseous state, may carry the other components of the hair care composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the hair care composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

E. Optional Ingredients

The hair care composition may further comprise one or more optional ingredients, including benefit agents Suitable benefit agents include, but are not limited to conditioning agents, cationic polymers silicone emulsions, anti-dandruff actives, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

1. Conditioning Agents

The conditioning agent of the hair care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference.

The hair care composition can comprise from about 0.01% to about 4%, alternatively from about 0.5% to about 3.5%, alternatively from about 0.5% to about 3% by weight of the hair care composition, of one or more silicone emulsions, wherein the silicone emulsion has a particle size of less than about 10 microns.

Suitable silicone emulsions can be selected from the group consisting of dimethiconol/dimethicone, silicone quaternium-22, silicone quaternium-17, silicone quaternium-80 micro-emulsion, and mixtures thereof.

The silicone conditioning agents suitable for use in the hair care compositions can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 10 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for suitable for use include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the hair care compositions may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

2. Emulsifiers

A variety of anionic and nonionic emulsifiers can be used in the hair care compositions. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

3. Chelating Agents

The hair care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Levels of the EDDS chelant in the hair care compositions can be as low as about 0.01 wt % or even as high as about 10 wt %, but above the higher level (i.e., 10 wt %) formulation and/or human safety concerns may arise. The level of the EDDS chelant may be at least about 0.05 wt %, at least about 0.1 wt %, at least about 0.25 wt %, at least about 0.5 wt %, at least about 1 wt %, or at least about 2 wt % by weight of the hair care composition. Levels above about 4 wt % can be used but may not result in additional benefit.

4. Anti-Dandruff Actives

Anti-dandruff agents suitable for use in hair care compositions include pyridinethione salts, azoles (e.g., ketoconazole, econazole, and elubiol), selenium sulfide, particulate sulfur, salicylic acid, and mixtures thereof. A typical anti-dandruff agent is pyridinethione salt. Hair care compositions can also include a zinc-containing layered material. An example of a zinc-containing layered material can include zinc carbonate materials. Of these, zinc carbonate and pyridinethione salts (particularly zinc pyridinethione or "ZPT) are common in the composition, and often present together.

5. Aqueous Carrier

The hair care compositions can be in the form of pourable liquids (under ambient conditions). Such compositions will therefore typically comprise a carrier, which is present at a level of from about 40% to about 80%, alternatively from about 45% to about 75%, alternatively from about 50% to about 70% by weight of the hair care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

Carriers useful in the hair care compositions include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Aerosol Foam Dispenser

The aerosol foam dispenser may comprise a reservoir for holding the hair treatment composition. The reservoir may be made out of any suitable material selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. There may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

Product Form

The hair care compositions may be presented in typical hair care formulations. They may be in the form of solutions, dispersion, emulsions, powders, talcs, encapsulated, spheres, spongers, solid dosage forms, foams, and other delivery mechanisms. The compositions may be hair tonics, leave-on hair products such as treatment, and styling products, rinse-off hair products such as shampoos and personal cleansing products, and treatment products; and any other form that may be applied to hair.

The hair care composition in the form of a foam can have a density of from about 0.025 g/cm$^3$ to about 0.30 g/cm$^3$, alternatively from about 0.05 g/cm$^3$ to about 0.20 g/cm$^3$, and alternatively from about 0.075 g/cm$^3$ to about 0.15 g/cm$^3$.

Test Methods

A. Cone/Plate Viscosity Measurement:
The viscosities of the examples are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of 2 s$^{-1}$ and at temperature of 26.5° C. The sample size is 2.5 ml and the total measurement reading time is 3 minutes.

B. cSt Viscosity Method
The hair care composition has a viscosity of from about 10 cSt to about 500 cSt, alternatively from about 15 cSt to about 400 cSt, alternatively from about 20 cSt to about 300 cSt, alternatively from about 25 cSt to about 250 cSt, and alternatively from about 30 cSt to about 250 cSt.

The cSt viscosity of the hair care composition is calculated using the following method:
Combine ingredients including surfactants, perfumes, viscosity reducing agents, polymers, other ingredients and the aqueous medium in a vessel. Samples are vortexed and placed into oven at 60° C. overnight to form a homogeneous solution. Samples that show hazing or clouding and formulas that appear macroscopically heterogeneous (e.g. multiple layers) at room temperature are not considered for further analysis and evaluation.

The cSt viscosities of the formulations are measured with calibrated viscometers (Size 200/350/450) from Cannon Instrument Company (2139 High Tech Road, State College, Pa., USA, 16803). Prior to the measurement, the formulations are equilibrated in the viscometer reservoir for 30 min at 40° C. in water bath to ensure a homogeneous temperature is reached in the system.

After the equilibration, the formulations are drawn to reach the starting mark with a rubber suction bulb and the flow time between the starting mark and end mark is recorded for calculation. Each formulation is measured three times to calculate average and standard deviation. Between samples, the viscometer is cleaned with water and acetone to rinse off residual.

cSt Viscosities are calculated based on the equation:

$$\text{Viscosity}(mm^2/s \cdot (cSt)) = \text{Time}(s) * \text{Constant}(mm^2/s^2 \cdot (cSt/s))$$

The time in the above equation is the flow time recorded in the experiment and the constants for each calibrated viscometer are obtained from the manuals.

C. Hair Wet Feel Friction Measurement:
A switch of 4 grams general population hair at 8 inches length is used for the measurement. Water temperature is set at 100° F., hardness is 7 grain per gallon, and flow rate is 1.6 liter per minute. For shampoos in liquid form, 0.2 ml of a liquid shampoo is applied on the hair switch in a zigzag pattern uniformly to cover the entire hair length, using a syringe. For shampoo in aerosol foam form, foam is dispensed to a weighing pan through an aluminum can of 53×190 mm size from CCL container. 0.2 gram of foam shampoo is applied on the hair switch uniformly to cover the entire hair length via a spatula. The hair switch is then 1st lathered for 30 seconds, rinse with water for 30 seconds, and 2nd lathered for 30 seconds. Water flow rate is then reduced to 0.2 liter per minute. The hair switch is sandwiched with a clamp under 1200 gram of force and pulled through the entire length while the water is running at the low flow rate. The pull time is 30 second. Friction is measured with a Friction analyzer with a load cell of 5 kg. Repeat the pull under rinse for total of 21 times. Total 21 Friction values are collected. The hair wet Feel Friction of shampoo reported here is the final rinse friction which is the average friction of the last 7 points.

D. Hair Dry Feel Friction Measurement
The shampooed and rinsed hair switch is air dried and placed between artificial skin surrogates. Dry feel friction (peak sum–static friction) is measured using a Texture Analyzer by applying a constant pressure of 60 psi to rub the hair switch a forward and reverse direction.

Examples

The following examples illustrate embodiments of the invention described herein. The exemplified hair care compositions may be made by conventional formulation and mixing techniques or by mixing together water and surfactants along with any solids that need to be melted at an elevated temperature, e.g. about 75° C. The ingredients are mixed thoroughly at the elevated temperature and then cooled to ambient temperature. Additional ingredients, including electrolytes, polymers, silicone emulsions, preservatives and fragrances may be added to the cooled product. It will be appreciated that other modifications of the hair care compositions, and/or conditioner compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of Hair Care compositions described herein.

TABLE 1

Examples and results of hair care compositions

| Ingredient | Ex1 | Ex2 | Ex3 | Ex21 | Ex4 | Ex5 | Ex6 | Ex7 | Ex8 | Ex9 | Ex10 | Ex11 | Ex12 |
|---|---|---|---|---|---|---|---|---|---|---|---|---|---|
| Wet Feel Friction | | 2105 | 1911 | | | 1327 | | | | | | | |
| Dry Feel Friction | | 1852 | 1852 | | | 1526 | | | | | | | |
| Bulk Viscosity (cps) | Phase separation | 395 | 773 | 839 | 919 | 460 | Phase separation | 6652 | 751 | 1073 | 662 | 582 | 1062 |
| Water | q.s. | q.s. | q.s. | q.s. | q.s. | q.s. | q.s. | q.s. | q.s. | q.s. | q.s. | q.s. | q.s. |
| Sodium Laureth Sulfate (SLE1S-70% active) [1] | 15 | 15 | 15 | 15 | 24 | 15 | 15 | 26 | 18.2 | 26 | 18.2 | 18.2 | 18.2 |
| Sodium Laureth Sulfate (SLE1S-26% active) [2] | 9 | 9 | 9 | 9 | — | 9 | 9 | — | 7.8 | — | 7.8 | 7.8 | 7.8 |
| Cocoamdopropyl Betaine (CAPB 30% active)[3] | 4 | 4 | 4 | 4 | 4 | 4 | 4 | 8 | 4 | 4 | 4 | 4 | 4 |
| Coco monoethanolamide (CMEA 85% active)[4] | — | — | — | — | — | — | — | — | — | — | — | — | — |
| Lauryl Hydroxysultaine (LHS 42.5% active)[5] | 4 | 4 | 4 | 4 | 4 | 4 | 4 | — | 4 | 4 | 4 | 4 | 4 |
| Para-hydroxyphenyl butanone[6] | — | — | — | — | — | — | — | — | — | — | — | — | — |
| Dipropylene Glycol | — | 10 | 10 | 7.5 | 10 | 10 | 10 | 10 | 10 | 10 | 10 | 10 | 10 |
| Guar, Hydroxylpropyl Trimonium Chloride, Jaguar C-500[7] | — | — | 0.4 | 0.4 | 0.4 | 0.4 | — | 0.4 | 0.4 | 0.4 | 0.4 | 0.4 | 0.4 |
| Guar, Hydroxylpropyl Trimonium Chloride, N-Hance 3196[8] | — | — | — | — | — | — | 0.4 | — | — | — | — | — | — |
| Polyquatenrium [9] | — | — | — | — | — | 0.2 | — | — | — | — | 0.2 | — | — |
| Silicone DM5500[10] | — | — | — | — | — | — | — | — | — | — | — | — | 2 |
| Silicone quaternium [11] | — | — | — | — | — | 2 | — | — | — | — | 2 | 2 | — |
| Fragrance | 2.4 | 2.4 | 2.4 | 2.4 | 2.4 | 2.4 | 2.4 | 2.4 | 2.4 | 2.4 | 2.4 | 2.4 | 2.4 |
| Sodium Chloride[12] | | | | | Adjust as needed for viscosity | | | | | | | | |
| Preservatives, pH adjusters | | | | | Up to 1% | | | | | | | | |

TABLE 4

Examples of Aerosol Foam hair care compositions (Linear Anionic Surfactant)

| Ingredient | Ex13 | Ex14 | Ex15 | Ex16 | Ex17 | Ex18 | Ex19 | Ex20 | Ex21 | Ex22 | Ex23 |
|---|---|---|---|---|---|---|---|---|---|---|---|
| Bulk Viscosity (cps) | 773 | 839 | 919 | 919 | 460 | 1000 | 751 | 1073 | 662 | 582 | 1062 |
| Water | q.s. | q.s. | q.s. | q.s. | q.s. | q.s. | q.s. | q.s. | q.s. | q.s. | q.s. |
| Sodium Laureth Sulfate (SLE1S-70% active) [1] | 15 | 15 | 24 | 24 | 15 | 5 | 18.2 | 26 | 18.2 | 18.2 | 18.2 |
| Sodium Laureth Sulfate (SLE1S-26% active) [2] | 9 | 9 | — | — | 9 | 19.1 | 7.8 | — | 7.8 | 7.8 | 7.8 |
| Cocoamdopropyl Betaine (CAPB 30% active)[3] | 4 | 4 | 4 | 4 | 4 | — | 4 | 4 | 4 | 4 | 4 |
| Coco monoethanolamide (CMEA 85% active)[4] | — | — | — | — | — | 2.3 | — | — | — | — | — |
| Lauryl Hydroxysultaine (LHS 42.5% active)[5] | 4 | 4 | 4 | 4 | 4 | 3.6 | 4 | 4 | 4 | 4 | 4 |
| Para-hydroxyphenylbutanone [6] | — | — | — | — | — | 5 | — | — | — | — | — |
| Dipropylene Glycol | 10 | 7.5 | 10 | 10 | 10 | — | 10 | 10 | 10 | 10 | 10 |
| Guar, Hydroxylpropyl Trimonium Chloride, Jaguar C-500[7] | 0.4 | 0.4 | 0.4 | 0.4 | 0.4 | — | 0.4 | 0.4 | 0.4 | 0.4 | 0.4 |
| Guar, Hydroxylpropyl Trimonium Chloride, N-Hance 3196[8] | — | — | — | — | — | — | — | — | — | — | — |

TABLE 4-continued

Examples of Aerosol Foam hair care compositions (Linear Anionic Surfactant)

| Ingredient | Ex13 | Ex14 | Ex15 | Ex16 | Ex17 | Ex18 | Ex19 | Ex20 | Ex21 | Ex22 | Ex23 |
|---|---|---|---|---|---|---|---|---|---|---|---|
| Polyquatenrium[9] | — | — | — | — | 0.2 | — | — | — | 0.2 | — | — |
| Silicone DM5500[10] | — | — | — | — | — | — | — | — | — | — | 2 |
| Silicone quaternium[11] | — | — | — | — | 2 | — | — | — | 2 | 2 | — |
| Fragrance | 2.4 | 2.4 | 2.4 | 2.4 | 2.4 | 1.6 | 2.4 | 2.4 | 2.4 | 2.4 | 2.4 |
| Sodium Chloride[12] | Adjust as needed for viscosity | | | | | | | | | | |
| Preservatives, pH adjusters | Up to 1% | | | | | | | | | | |
| Propellant A46[13] | 4 | 4 | 4 | — | 4 | 4 | 4 | 4 | 4 | 4 | 4 |
| Propellant A70[14] | — | — | — | 4 | — | — | — | — | — | — | — |

[1] Sodium Laureth (1 molar ethylene oxide) sulfate at 70% active, supplier: Stephan Co
[2] Sodium Laureth (1 molar ethylene oxide) sulfate at 26% active, supplier: P&G
[3] Tegobetaine F-B, 30% active, supplier: Goldschmidt Chemical
[4] Coco monethanolamide at 85% active, supplier: Stephan Co or supplier Evonik
[5] LHS (Mackam LHS) at 42.5% active level, supplier: Rhodia
[6] Raspberry Ketone, supplier: Spectrum
[7] Jaguar C500, MW of 500,000, CD of 0.8, from Rhodia
[8] N-Hance 3196, MW of 1,100,000, CD of 0.8, from Ashland
[9] Polydadmac, trade name: Mirapol 100s, from Rhodia
[10] Silicone emulsion, 42% active, from Wacker
[11] Silicone quaternium micro-emulsion, 30% active, Abil ME 45, from Evonik
[12] Sodium Chloride USP (food grade) from Morton
[13] Aeron A-Blends, A46 (Isobutane/Propane ratio = 84.85/15.15) from Diversified CPC International
[14] Aeron A-Blends, A70 (Isobutane/Propane ratio = 57.11/42.89) from Diversified CPC International

What is claimed is:

1. An aerosol hair care composition comprising:
   a. a surfactant system consisting of:
      i) from about 20% to about 28% of sodium laureth-1 sulfate;
      ii) from about 8% to about 13% of a mixture of cocamidopropyl betaine and lauryl hydroxysultaine;
   b. from about 7% to about 10% by weight dipropylene glycol;
   c. from about 0.05% to about 1% by weight of guar hydroxypropyl trimonium chloride and
   d. from about 1% to about 10% by weight of a propellant;
   wherein the aerosol hair care composition is a shampoo.

2. The hair care composition of claim 1, further comprising from about 0.01 to about 4% of one or more silicone emulsion, wherein said silicone has a particle size less than about 10 micrometers.

3. The hair care composition of claim 1, having from about 0.05% to about 0.9% by weight of the guar hydroxypropyl trimonium chloride.

4. The hair care composition of claim 1, further comprising an anti-dandruff active.

* * * * *